United States Patent
Goldman et al.

(10) Patent No.: US 7,319,142 B1
(45) Date of Patent: Jan. 15, 2008

(54) **NUCLEOTIDE AND AMINO ACID SEQUENCES FROM *XENORHABDUS* AND USES THEREOF**

(75) Inventors: Barry S. Goldman, St. Louis, MO (US); Karina Krasomil-Osterfeld, Ellisville, MO (US); Thomas M. Malvar, North Stonington, CT (US); John W. Pitkin, Wildwood, MO (US); Steven C. Slater, Middleton, WI (US); Wei Wu, St. Louis, MO (US); Jiamin Zeng, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/216,782

(22) Filed: Aug. 31, 2005

Related U.S. Application Data

(60) Provisional application No. 60/606,098, filed on Aug. 31, 2004.

(51) Int. Cl.
*C07H 21/04* (2006.01)
*C07K 14/00* (2006.01)

(52) U.S. Cl. ................ 536/23.1; 530/350
(58) Field of Classification Search ............... None
See application file for complete search history.

(56) References Cited

U.S. PATENT DOCUMENTS 6,048,838 A * 4/2000 Ensign et al. ............ 514/2

OTHER PUBLICATIONS

☐☐ Khandelwal et al., Insecticidal Activity Associated with the Outer Membrane Vesicles of *Xenorhabdus nematophilus*, Applied and Environmental Microbiology, Apr. 2003, vol. 69, No. 4, pp. 2032-2037.*

* cited by examiner

*Primary Examiner*—Robert B. Mondesi
(74) *Attorney, Agent, or Firm*—Timothy K. Ball; Arnold & Porter LLP

(57) ABSTRACT

The invention provides isolated nucleotide sequences from *Xenorhabdus nematophila* species Xs86068, and, in particular, nucleotide sequences that encode insect inhibitory proteins, the insecticidal proteins, and compositions that comprise one or more of the insecticidal proteins for use in controlling insect infestation.

3 Claims, No Drawings

NUCLEOTIDE AND AMINO ACID SEQUENCES FROM *XENORHABDUS* AND USES THEREOF

CROSS REFERENCE TO RELATED APPLICATIONS

This application claims the benefit of priority to U.S. Provisional Application 60/606,098 filed Aug. 31, 2004.

BACKGROUND OF THE INVENTION

The present invention relates to nucleic acid sequences from *Xenorhabdus nematophila*. The invention also relates to methods of using the disclosed nucleic acid molecules to encode proteins and fragments of proteins and to develop antibodies, for example, for nucleic acid sequence identification and analysis, preparation of constructs, transformation of cells such as bacterial cells and plant cells with the nucleotide compositions disclosed herein to produce *Xenorhabdus* proteins or fragments thereof, in particular novel insect inhibitory, bactericidal, fungicidal and nematocidal proteins.

*Xenorhabdus* is a Gram-negative bacterium, a member of the family of Enterobacteriaceae, and symbiotically associated with nematodes of the genus *Steinernema*. The nematode-bacterial complex can be characterized as an obligate and lethal parasitic relationship, specializing in parasitizing and proliferating in soil insect larvae. Infective, non-feeding stages of these nematodes live in soil and carry in their gut the nematode-genus-specific symbiotic bacteria. It is believed that the nematodes actively search for the appropriate insect host, invade the insect larvae through natural openings or lesions in the cuticle and, once inside the hemolymph, release their symbiotic bacteria. The nematode-bacterial complex secretes a variety of highly efficient extracellular metabolites and proteins exhibiting insecticidal, bactericidal, fungicidal and nematocidal properties to secure the larval mass as a source of nutrition. An array of extracellular enzymes such as lipases, phospholipases, proteases, nucleases as well as several broad spectrum antibiotics, and antifungal and nematocidal compositions are also secreted [Boemare & Akhurst, J. Gen. Microbiol. 134: 751-761, 1988; Li et al., Can. J. Microbiol. 43(8):770-773, 1997; McInerney et al., J. Nat. Prod. 54(3):774-84, 1991; McInerney et al., J. Nat. Prod. 54(3):785-95, 1991; Sundar and Chang, J. Gen. Microbiol. 139 (Pt 12):3139-48, 1993]. It has been discovered that some compounds secreted by *Xenorhabdus* exhibit anti-neoplastic (U.S. Pat. No. 5,827, 872), acaricidal, anti-inflammatory and anti-ulcerogenic properties (U.S. Pat. No. 4,837,222). U.S. Pat. No. 6,048, 838 describes insect inhibitory proteins that exhibit a molecular weight of greater than 100 kDa produced by *Xenorhabdus* sp., which are active against a variety of insect species including the orders, Lepidoptera, Coleoptera, Diptera, and Acarina, when provided in the insect diet.

*Xenorhabdus* strains have been shown to produce an array of extracellular proteins and small molecules or secondary metabolites having specialized functions [Li et al., Can. J. Microbiol. 43(8):770-773, 1997; McInerney et al., J. Nat. Prod. 54(3):774-84, 1991; U.S. Pat. No. 6,048,838]. More commercially interesting are proteins and small molecules having antibiotic properties or proteins that exhibit insect inhibitory activity. A small number of insect inhibitory proteins have previously been identified from these bacteria, symbionts of insect-parasitic nematodes (Morgan et al., Appl. Environ. Microbiol., 67(5):2062-2069, 2001; U.S. Pat. No. 6,048,838). Such proteins and compositions are used as biologically safe and effective pest control agents. Unlike chemical pesticide compositions, these proteins have no effect upon the environment in general, can be targeted to direct their effect primarily upon target insect species, and have no effect on non-target species. Therefore, a different resistance management strategy that takes advantage of insect inhibitory proteins derived from distinct microbial sources other than *B. thuringiensis* would be desirable. Insect inhibitory proteins isolated from *Xenorhabdus* bacteria seem to have all the prerequisites for the delivery of novel genes for transgenic expression of insect pest inhibiting proteins to provide pest resistance to plants, either alone or in combination with *Bacillus thuringiensis* insecticidal proteins.

Therefore, there is a great deal of interest in identifying the genes that encode new insect inhibiting proteins, and proteins involved in the biosynthetic pathways of novel antibiotics produced by *Xenorhabdus* bacteria, as well as other useful proteins. Isolation and sequencing of the entire genome of *Xenorhabdus* would facilitate such an endeavor, because it would allow dissection and analysis of the genome into discrete genes encoding proteins having beneficial properties as described herein.

SUMMARY OF THE INVENTION

In one embodiment, the present invention provides isolated nucleotide sequences from *Xenorhabdus nematophila* bacterium, strain Xs86068. The isolated nucleotide sequences encode at least a group of insect inhibitory proteins that have insecticidal activities against insect pests. The insect inhibitory proteins of the present invention comprises, but are not limited to, the following amino acid sequences: SEQ ID NO:6903, SEQ ID NO:6904, SEQ ID NO:6905, SEQ ID NO:7110, SEQ ID NO:7179, SEQ ID NO:7514, SEQ ID NO:7776, SEQ ID NO:7777, SEQ ID NO:7803, SEQ ID NO:8275, SEQ ID NO:8277, SEQ ID NO:8279, SEQ ID NO:8280, SEQ ID NO:8281, SEQ ID NO:8454, SEQ ID NO:8468, SEQ ID NO:8595, SEQ ID NO:9946, SEQ ID NO:10477, SEQ ID NO:10481, SEQ ID NO:10482, SEQ ID NO:10483, SEQ ID NO:10484, SEQ ID NO:10485, SEQ ID NO:10486, SEQ ID NO:10487, SEQ ID NO:10488, SEQ ID NO:10551, SEQ ID NO:11147, SEQ ID NO:11688, SEQ ID NO:11690, SEQ ID NO:11691, SEQ ID NO:11692, and SEQ ID NO:11693. The insecticidal activities are manifested by inhibiting the growth or development of, or contributing substantially to the death of, an insect from the insect orders Coleoptera [e.g., western corn rootworm (WCR, *Diabrotica virgifera virgifera* LeConte), and cotton boll weevil (BWV, *Anthomonas grandis grandis*), and Hemiptera [e.g., Western Tarnished Plant Bug (WTPB, *Lygus hesperus* Knight)]. The present insect inhibitory proteins also have insecticidal activities against insect pests from other insect orders such as Diptera and Hymenoptera and against sucking and piercing insects or insect larvae.

The isolated nucleotide sequences of the present invention that encode the insect inhibitory proteins comprise, but are not limited to, the following: SEQ ID NO:795, SEQ ID NO:796, SEQ ID NO:797, SEQ ID NO:1002, SEQ ID NO:1071, SEQ ID NO:1406, SEQ ID NO:1668, SEQ ID NO:1669, SEQ ID NO:1695, SEQ ID NO:2167, SEQ ID NO:2169, SEQ ID NO:2171, SEQ ID NO:2172, SEQ ID NO:2173, SEQ ID NO:2346, SEQ ID NO:2360, SEQ ID NO:2487, SEQ ID NO:3838, SEQ ID NO:4369, SEQ ID NO:4373, SEQ ID NO:4374, SEQ ID NO:4375, SEQ ID NO:4376, SEQ ID NO:4377, SEQ ID NO:4378, SEQ ID NO:4379, SEQ ID NO:4380, SEQ ID NO:4443, SEQ ID NO:5039, SEQ ID NO:5580, SEQ ID NO:5582, SEQ ID NO:5583, SEQ ID NO:5584 and SEQ ID NO:5585.

In another embodiment, the present invention provides purified insect inhibitory proteins from *Xenorhabdus nematophila* bacterium, strain Xs86068, which are active against insect pests. The insect inhibitory proteins of the present invention at least comprises, but are not limited to, the following amino acid sequences: SEQ ID NO:6903, SEQ ID NO:6904, SEQ ID NO:6905, SEQ ID NO:7110, SEQ ID NO:7179, SEQ ID NO:7514, SEQ ID NO:7776, SEQ ID NO:7777, SEQ ID NO:7803, SEQ ID NO:8275, SEQ ID NO:8277, SEQ ID NO:8279, SEQ ID NO:8280, SEQ ID NO:8281, SEQ ID NO:8454, SEQ ID NO:8468, SEQ ID NO:8595, SEQ ID NO:9946, SEQ ID NO:10477, SEQ ID NO:10481, SEQ ID NO:10482, SEQ ID NO:10483, SEQ ID NO:10484, SEQ ID NO:10485, SEQ ID NO:10486, SEQ ID NO:10487, SEQ ID NO:10488, SEQ ID NO:10551, SEQ ID NO:11147, SEQ ID NO:11688, SEQ ID NO:11690, SEQ ID NO:11691, SEQ ID NO:11692, and SEQ ID NO:11693.

In still another embodiment, the present invention provides an insecticidal composition that comprises one or more insect inhibitory proteins as specified above having an amino acid sequence selected from the group consisting of SEQ ID NO:6903, SEQ ID NO:6904, SEQ ID NO:6905, SEQ ID NO:7110, SEQ ID NO:7179, SEQ ID NO:7514, SEQ ID NO:7776, SEQ ID NO:7777, SEQ ID NO:7803, SEQ ID NO:8275, SEQ ID NO:8277, SEQ ID NO:8279, SEQ ID NO:8280, SEQ ID NO:8281, SEQ ID NO:8454, SEQ ID NO:8468, SEQ ID NO:8595, SEQ ID NO:9946, SEQ ID NO:10477, SEQ ID NO:10481, SEQ ID NO:10482, SEQ ID NO:10483, SEQ ID NO:10484, SEQ ID NO:10485, SEQ ID NO:10486, SEQ ID NO:10487, SEQ ID NO:10488, SEQ ID NO:10551, SEQ ID NO:11147, SEQ ID NO:11688, SEQ ID NO:11690, SEQ ID NO:11691, SEQ ID NO:11692, and SEQ ID NO:11693. The insecticide composition disclosed herein may comprise one of the following: insecticidal protein suspensions, isolated protein components or bacterial cells that are transformed with one or more nucleotide sequences that encode the insecticidal inhibitory proteins of the invention. The insecticidal composition may be formulated in the form of a dust, a granular material, an oil (vegetable or mineral) suspension, a water suspension, a mixture of oil and water emulsion, or a wettable powder, or in combination with an agriculturally acceptable carrier that may be solid or liquid.

In a further embodiment, the present invention provides an isolated *Xenorhabdus nematophila* bacterium, strain Xs86068. The inventors have demonstrated that this strain exhibits insecticidal activity against commercially important insect species including, e.g., those in the orders Coleoptera (e.g., WCR, BWV), and Hemiptera (e.g., WTPB). The strain may have insecticidal activity against other insects including, e.g., Dipteran and Hymenopteran insects, or a sucking and piercing insect or an insect larva thereof. The insect inhibitory proteins also have insecticidal activities against insect pests from other insect orders. This strain may be used as a source for DNA sequences encoding insecticidal proteins, and when formulated into a composition of matter as a spray, powder or emulsion, for the treatment of plants or animals to inhibit insect infestation. The Xs86068 strain was deposited on Jul. 26, 2004, with the Agriculture Research Culture Collection (NRRL) International Depository Authority at 1815 North University Street, in Peoria, Ill. 61604 U.S.A., according to the Budapest Treaty on the International Recognition of the Deposit of Microorganisms for the Purpose of Patent Procedures and was designated as NRRL B-30757.

The present invention relates to a plant cell, a mammalian cell, a bacterial cell other than a *X. nematophila* Xs86068 cell, an algal cell, an insect cell and a fungal cell transformed with an isolated nucleic acid molecule of the present invention that is selected from the group consisting of SEQ ID NO:795, SEQ ID NO:796, SEQ ID NO:797, SEQ ID NO:1002, SEQ ID NO:1071, SEQ ID NO:1406, SEQ ID NO:1668, SEQ ID NO:1669, SEQ ID NO:1695, SEQ ID NO:2167, SEQ ID NO:2169, SEQ ID NO:2171, SEQ ID NO:2172, SEQ ID NO:2173, SEQ ID NO:2346, SEQ ID NO:2360, SEQ ID NO:2487, SEQ ID NO:3838, SEQ ID NO:4369, SEQ ID NO:4373, SEQ ID NO:4374, SEQ ID NO:4375, SEQ ID NO:4376, SEQ ID NO:4377, SEQ ID NO:4378, SEQ ID NO:4379, SEQ ID NO:4380, SEQ ID NO:4443, SEQ ID NO:5039, SEQ ID NO:5580, SEQ ID NO:5582, SEQ ID NO:5583, SEQ ID NO:5584, and SEQ ID NO:5585. In an event when a bacterial cell is used, the bacterium may be selected from the group consisting of *Bacillus, Agrobacterium, Pseudomonas, Rhizobium, Erwinia, Azotobacter, Azospirillum, Klebsiella, Flavobacterium* and *Alcaligenes*.

Both the isolated nucleotide sequences and the amino acid sequences of the present invention are provided in the Sequence Listing file in electronic format that also includes other nucleotide and amino acid sequences, all of which are set forth in SEQ ID NO:1 through SEQ ID NO:16918, the electronic copy being included on the CD-ROM that accompanies this specification.

Various advantages and features of the present invention will become hereinafter apparent, and the nature of the invention may be more clearly understood, by reference to the following detailed description of the embodiments of the invention and to the appended claims.

BRIEF DESCRIPTION OF THE SEQUENCES

All the nucleotide and amino acid sequences as set forth in SEQ ID NO:1 through SEQ ID NO:16918 and as categorized below are provided in electronic format within the Sequence Listing file, the electronic copy being included on the CD-ROM that accompanies this specification.

SEQ ID NO:1 through SEQ ID NO:6108 are nucleotide sequences isolated from *X. nematophila* strain Xs86068. Each of these nucleotide sequences reside within a larger sequence referred to as a contig sequence, and are cross referenced in the SEQ LISTING file with reference to SEQ ID NO:'s corresponding to a particular contig sequence.

SEQ ID NO:6109 through SEQ ID NO:12216 represent amino acid sequences encoded by the nucleotide sequences as set forth at SEQ ID NO:1 through SEQ ID NO:6108, respectively. SEQ ID NO:6109 represents the amino acid sequence translation of SEQ ID NO:1, SEQ ID NO:6110 represents the amino acid sequence translation of SEQ ID NO:2, and so on and so forth.

SEQ ID NO:12217 through SEQ ID NO:14867 represent predicted promoter nucleotide sequences isolated from *X. nematophila* strain Xs86068.

SEQ ID NO:14868 through SEQ ID NO:16342 represent terminator nucleotide sequences isolated from *X. nematophila* strain Xs86068.

SEQ ID NO:16343 through SEQ ID NO:16424 represent nucleotide sequences isolated from *X. nematophila* strain Xs86068 encoding tRNA's and rRNA's.

SEQ ID NO:16425 through SEQ ID NO:16918 represent the contig sequences.

DETAILED DESCRIPTION OF THE INVENTION

In accordance with the present invention, novel nucleic acid molecules have been isolated from a bacterium *X. nematophila*, strain Xs86068, and their encoded polypeptides or proteins are provided. Isolated nucleic acid molecules comprising regulatory elements that include promoter and terminator sequences are also provided. In a preferred embodiment, the present invention provides isolated nucleic acid molecules that encodes a class of proteins that exhibits insect inhibitory activity, wherein the activity is manifested by inhibiting the growth or development of, or contributing substantially to, or causing the death of an insect, such as a Coleopteran, a Dipteran, a Lepidopteran, a Hemipteran, a Hymenopteran, or a sucking and piercing insect or insect larvae thereof. Therefore, those skilled in the art will find the utility of these insecticidal proteins in protecting plants from insect infestations.

The present invention also provides isolated nucleic acid molecules encoding other types of useful proteins and compositions, e.g., insect inhibitory proteins, microbial inhibitory proteins including bactericidal and fungistatic proteins, nematocidal and protein homologs of chitinases, histones and restriction enzymes, proteases, proteins capable of conferring resistance to heavy metals or other toxic compositions, polyketide synthases, among others.

The present invention relates to methods of obtaining the disclosed nucleic acid molecules and proteins and of using the disclosed nucleic acid molecules, proteins, fragments of proteins, and antibodies, for example, for gene identification and analysis, preparation of constructs, transformation of cells with nucleotide compositions disclosed herein to produce *Xenorhabdus* proteins or fragments thereof, in particular novel insect inhibitory, bactericidal, fungicidal and nematocidal proteins.

Three CD ROM diskettes are provided along with the application as filed including a first CD-ROM diskette containing the Sequence Listing as filed, this diskette being labeled as the CRF (computer readable form), and two additional CD-ROM diskettes each consecutively labeled as Copy 1 and Copy 2. There is a single file on each of these three diskettes. The CRF copy of the Sequence Listing and the Copy 1 and Copy 2 Sequence Listing are the same. Each diskette was produced using an IBM-PC type machine, using an MS-DOS operating system running MS-Windows. The Sequence Listing file was created on Aug. 5, 2005, and the diskettes were produced by writing the file to the diskettes on Aug. 31, 2005. The file on the diskettes was provided the filename "52053B Xeno Seq Listing.txt", the file is 28.005 megabytes in size, and is a text file that lists SEQ ID NO's sequentially from SEQ ID NO:1 through SEQ ID NO:16,918. The Sequence Listing is incorporated by reference into the specification in its entirety.

One aspect of the present invention relates to an isolated nucleic acid molecule having a nucleotide sequence, wherein: (1) the nucleotide sequence hybridizes under stringent conditions to a nucleotide sequence of a second isolated nucleic acid molecule selected from the group consisting of SEQ ID NO:1 through SEQ ID NO:6108 or complements thereof, (2) the nucleotide sequence is a portion of any sequence selected from the group consisting of SEQ ID NO:1 through SEQ ID NO:6108; or (3) the nucleotide sequence is the complement of (1) or (2).

The term "an isolated nucleic acid" refers to a nucleic acid that is no longer accompanied by some of materials with which it is associated in its natural state or to a nucleic acid the structure of which is not identical to that of any of naturally occurring nucleic acid. Examples of an isolated nucleic acid include: (1) DNAs which have the sequence of part of a naturally occurring genomic DNA molecules, but are not flanked by two coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid may also be comprised of one or more segments of cDNA, genomic DNA or synthetic DNA.

Stringent conditions are sequence dependent and will be different under various circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Appropriate stringent conditions are known to those skilled in the art or can be found in *Current Protocols in Molecular Biology*, John Wiley & Sons, N.Y. 6.3.1-6.3.6 (1989). For the purposes of this disclosure, stringent conditions include at least one wash (usually 2) in 0.2×SSC at a temperature of at least about 50° C., usually about 55° C., for 20 minutes, or equivalent conditions.

The hybridization portion of the two hybridizing nucleic acids is usually at least 50 nucleotides in length, more usually at least about 75 nucleotides in length, more particularly at least 100 nucleotides in lengths. The hybridizing portion of the hybridizing nucleic acid is at least 70%, at least 80%, at least 90%, or at least 98% identical to the sequence of a portion of a sequence as set forth in SEQ ID NO:1 to SEQ ID NO:6108.

Another aspect of the present invention relates to an isolated nucleic acid molecule comprising one or more open reading frames as set forth in SEQ ID NO:1 to SEQ ID NO:6108. An "open reading frame" (ORF) is a region of a nucleotide sequence that encodes a polypeptide. This region may represent a portion of a coding sequence or a total coding sequence. Open reading frames in genomic sequences can be screened for the presence of protein homologues utilizing one or a number of different search algorithms that have been developed, one example of which are the suite of programs referred to as BLAST programs. The open reading frames identified in the isolated nucleic acid molecules comprise SEQ ID NO:1 through SEQ ID NO:6108, wherein the open reading frames encode *Xenorhabdus* proteins or polypeptide or fragments thereof which are homologues of known proteins or unknown proteins. It has been discovered that the nucleic acids and amino acids encoded by the nucleic acids derived from *Xenorhabdus* species (bacteria commonly symbiotically associated with insect pathogenic nematodes) are surprisingly useful in providing compositions comprising insect inhibitory proteins, microbial inhibitory proteins including bactericidal, bacteriostatic, fungicidal, and fungistatic proteins, protein homologs of chitinases, histones and restriction enzymes, proteases, proteins capable of conferring resistance to heavy metals or other toxic compositions, proteins and compositions capable of conferring pharmaceutical advantages such as antineoplastic, acaricidal, anti-inflammatory and anti-ulcerogenic properties, polyketide synthases, transposons and mobile genetic elements and their corresponding transposases, excisases, integrases, and invertases, phage and phage particle proteins, other useful proteins homologous to proteins derived from *Xenorhabdus, Photorhabdus, Serratia, Yersinia, Salmonella, E. coli*, and *Erwinia* sp. among others. In addition, antibodies directed to the above-mentioned proteins and fragments thereof have been discovered to be of particular utility in the present invention. The invention also relates to methods of using the disclosed nucleic acid molecules, proteins, fragments of proteins, and antibodies, for example, for nucleotide sequence identification and analysis, preparation of constructs, transformation of cells with nucleotide compositions disclosed herein to produce *Xenorhabdus* proteins or fragments thereof, in particular novel insect inhibitory, bactericidal and fungicidal proteins.

The present invention provides an isolated nucleic acid molecule comprising a nucleotide sequence, wherein: (1) the nucleotide sequence hybridizes under stringent conditions to a nucleotide sequence of a second isolated nucleic acid molecule, wherein the hybridizing portion of the nucleotide sequence of the second isolated nucleic acid molecule encodes a polypeptide or protein having an amino acid sequence selected from the group consisting of SEQ ID NO:6109 to SEQ ID NO:12216; (2) the nucleotide sequence encodes a polypeptide or protein, wherein the amino acid sequence of the polypeptide or protein is substantially identical to any one set forth in SEQ ID NO:6109 to SEQ ID NO:12216; or (3) the nucleotide sequence is the complement of (1) or (2). In one embodiment, the nucleotide sequence is or is a portion of the isolated nucleic acid molecule as disclosed herein, selected from the group consisting of SEQ ID NO:1 to SEQ ID NO:6108. The present invention provides an isolated protein having an amino acid sequence that is substantially identical to a member selected from group consisting of SEQ ID NO:6109 through SEQ ID NO:12216. By "substantially identical" or "substantial identity" as used in reference to two amino acid sequences, it is meant that one amino acid sequence is identical to the other amino acid sequence or has at least 50% sequence identity, at least 70% sequence identity, preferably at least 80%, more preferably at least 90%, and most preferably at least 95% identity when compared to the other amino acid sequence as a reference sequence using the programs described herein, preferably BLAST using standard parameters, as described below. "Sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Polypeptides that are substantially similar share sequences in which residue positions are not identical and may differ by conservative amino acid changes. Conservative amino acid substitutions refer to the interchangeability of residues having similar side chains. "Conservative amino acid substitutions" refer to substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs.

Optimal alignment of sequences for comparison can use any means to analyze sequence identity (homology) known in the art, e.g., by FGENESB (Softberry, Inc., Mount Kisco, N.Y.) that is based on Markov chain models of coding regions and translation and termination sites, by the BLAST algorithm (Altschul et al, J. Mol. Biol. 215: 403-410, 1990) that is suitable for determining sequence similarity; by the progressive alignment method of termed "PILEUP" (Morrison, Mol. Biol. Evol. 14:428-441, 1997); or by the local homology algorithm of Smith & Waterman (Adv. Appl. Math. 2: 482, 1981). One skilled in the art will recognize that a value of sequence identity can be appropriately adjusted to determine corresponding sequence identity of two nucleotide sequences encoding the proteins of the present invention by taking into account codon degeneracy, conservative amino acid substitutions, reading frame positioning and the like. Substantial identity of nucleotide sequences for these purposes normally means sequence identity of at least 50%, preferably at least 60%, more preferably at least 70%, more preferably at least 80%, more preferably at least 90%, and most preferably at least 95%. The present invention also includes an isolated nucleic acid comprising a nucleotide sequence encoding a polypeptide having an amino acid sequence set forth in any of SEQ ID NO:6109 to SEQ ID NO:12216 with conservative amino acid substitutions.

In a preferred embodiment of the present invention, the isolated nucleic acid molecule comprising a nucleotide sequence encodes an insect inhibitory protein. The nucleotide sequence encodes all or substantial portion of a polypeptide the amino acid sequence of which is substantially identical to one of the sequences as set forth in SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693, wherein the nucleotide sequence is selected from the group consisting of SEQ ID NO's:795, 796, 797, 1002, 1071, 1406, 1668, 1669, 1695, 2167, 2169, 2171, 2172, 2173, 2346, 2360, 2487, 3838, 4369, 4373, 4374, 4375, 4376, 4377, 4378, 4379, 4380, 4443, 5039, 5580, 5582, 5583, 5584 and 5585. The phrase "an insecticidal protein" or "an insect inhibitory protein" refers to any polypeptide or protein or a substantial portion thereof that exhibits insect inhibitory activity, wherein the activity is manifested by inhibiting the growth or development of, or contributing substantially to, or causing the death of a Coleopteran, a Dipteran, a Lepidopteran, a Hemipteran, a Hymenopteran, or a sucking and piercing insect or insect larvae thereof. It also refers to any polypeptide or protein with modified amino acid sequence, such as sequence which has been mutated, truncated, increased and the like and which maintains at least the insect inhibitory activity associated with the native protein. Accordingly, the isolated nucleic acids encoding those polypeptide or protein with such modification are also within the scope of the present invention.

The insect inhibitory proteins of the present invention may share some homology to known insecticidal proteins. For instance, the polypeptide sequence as set forth in SEQ ID NO: 6903 exhibits 71% amino acid sequence homology to an insecticidal toxin complex protein TccB2 from *Photorhabdus luminescens laumondii*. The polypeptide sequence as set forth in SEQ ID NO: 6905 exhibits 61% amino acid sequence homology to an insecticidal toxin complex protein TccA2 from *Photorhabdus luminescens laumondii*. The polypeptide sequence as set forth in SEQ ID NO: 7110 exhibits 57% amino acid sequence homology to an insecticidal toxin complex protein TccC from *Photorhabdus luminescens laumondii*, etc.

In another aspect of the present invention, the isolated nucleic acid molecule encodes all or a portion of a protein homologue to a known protein and may have important utility. For example, the isolated nucleic acid molecule encodes all or a portion of a hemolysin lipase protein homologue wherein the amino acid sequence of the protein homologue is substantially identical to one of the sequences as set forth in SEQ ID NO's: 6531, 6578, 6696, 7505, 7679, 7793, 7939, 8216, 8220, 8222, 8366, 8745, 9199, 9212, 10143, 10306, 10325, 10683, 10919, 10995, 10996, 11246, 11991 and 12000.

The isolated nucleic acid molecule comprising a nucleotide sequence encodes all or a portion of a polyketide synthase homologue, wherein the amino acid sequence of the protein homologue is substantially identical to one of the sequences as set forth in SEQ ID NO's: 7253, 8852, 8857, 8864, 9558, 9560, 11014, 11583, 11587, 12090 and 12112. Polyketides are small bioactive molecules that are a class of small compounds linked by their biosynthetic pathways. The pathways and their products are particularly abundant in soil microorganisms including *Xenorhabdus nematophila*. A large number of major pharmaceutical and agricultural products have been derived from these complex natural products including insecticides, fungicides, antibacterials, anti-inflammatory, cancer-fighting agents, and cholesterol-lowering agents. Examples of polyketides include Rifamycins (Rifampin), Adriamycin (Doxorubicin), Erythromycin, Mevacor (Lovastatin), Ascomycin (Immunomycin), and Spinosad. Polyketides are produced by large proteins called synthases (or synthetases). There are an extraordinary number of polyketides synthases from *Xenorhabdus*. In addition to polyketide synthases *Xenorhabdus* also contains an extraordinary number of related proteins called non-ribosomal peptide synthases (NRP synthase). These proteins also generate small molecules with a variety of biochemical functions. It is possible that any of these genes can be placed into the genome of a plant and produces a substance (polyketide or non-ribosomal peptide) that can protect a plant against damage from insects, fungi, or bacteria. In addition, these genes can be placed in plants to generate polyketides or non-ribosomal peptide for other uses including pharmaceuticals.

The isolated nucleic acid molecule comprising a nucleotide sequence encodes all or a portion of a protease homologue, wherein the amino acid sequence of the protein homologue is substantially identical to one of the sequences as set forth in SEQ ID NO's: 6308, 6309, 6310, 6393, 6537, 6549, 6595, 6774, 6941, 6942, 7199, 7289, 7328, 7503, 7627, 7682, 7683, 7749, 8152, 8300, 8301, 8870, 8957, 9108, 9263, 9265, 9296, 9319, 9343, 9720, 9725, 9748, 9749, 9884, 10246, 10385, 10461, 10588, 10614, 10896, 11020, 11830, 11831 and 11901. Protease plays very important roles in an organism's metabolism and proteins synthesis and several types of proteases have been reported. A processing protease is a protease that cleaves a propeptide to generate a mature biochemically active polypeptide (Enderlin and Ogrydziak, Yeast 10:67-79, 1994). Serine protease is required for intramitochondrial proteolysis and maintenance of respiratory function. Ubiquitin-specific protease (ubiquitin C-terminal hydrolase) of the 26S proteasome complex is involved in vacuole biogenesis and osmoregulation. Inner membrane protease of mitochondria acts in complex with IMP1P but has different substrate specificity for removal of signal peptidase serine protease of the subtilisin family with broad proteolytic specificity (U.S. Pat. No. 6,723,837). Therefore, the nucleotide sequences may find utility for those skilled in the art in generating useful traits in plants or other organisms using available techniques.

The isolated nucleic acid molecule comprising a nucleotide sequence encodes all or a portion of a chitinase homologue, wherein the amino acid sequence of the protein homologue is substantially identical to one of the sequences as set forth in SEQ ID NO's: 6902, 6906, 7325, 8047 and 10542. The genes encoding these protein homologues may be overexpressed in plants as antifungal proteins to control fungal diseases in plants. A chitinase is one of several classes of antifungal proteins identified that include chitinases, defensins, cysteine-rich chitin-binding proteins, β-1,3-glucanases, permatins (including zeamatins), thionins, ribosome-inactivating proteins, and non-specific lipid transfer proteins (U.S. Pat. No. 6,573,361).

The isolated nucleic acid molecule comprising a nucleotide sequence encodes all or a portion of a restriction enzyme homologue, wherein the amino acid sequence of the protein homologue is substantially identical to one of the sequences as set forth in SEQ ID NO's: 8941, 8945, 9353, 11041, 11042, 11113 and 11114. "Restriction enzyme" refers to an enzyme that recognizes a specific palindromic sequence of nucleotides in double stranded DNA and cleaves both strands. Cleavage typically occurs within the restriction site. It is obvious to those skilled in the art about the utility of these nucleotide sequences encoding the restrictions enzyme homologues.

The isolated nucleic acid molecule comprising a nucleotide sequence encodes all or a portion of a histone homologue, wherein the amino acid sequence of the protein homologue is substantially identical to one of the sequences as set forth in SEQ ID NO's: 6182, 7457, 7980, 8272, 8605, 8765, 8778, 8861, 9590, 9802, 10293, 10449, 10469, 10762, 10812, 10926, 11206, 11677 and 12135. Histones were not previously found in bacteria. However, histones are abundant and required for DNA organization in all eukaryotes. Genes with homology to histones and proteins that affect histones, such histone deacetylases may affect histones in insects, disrupting normal cellular processes.

The isolated nucleic acid molecule comprising a nucleotide sequence encodes all or a portion of a ferritin homologue the amino acid sequence of which is substantially identical to one of the sequences as set forth in SEQ ID NO's: 6267, 6268 and 9272. These proteins may be used for overexpression in plants may result in an increase of resistance to abiotic and biotic oxidative stresses. Overexpression of ferritin promotes cellular productivity during limited water conditions to prevent formation of oxygen radicals (US Pat. Appl. Pub. No. 20030233670).

The isolated nucleic acid molecule comprising a nucleotide sequence encodes all or a portion of a drug metabolite transporter protein homologue, the amino acid sequence of which is substantially identical to one of the sequences as set forth in SEQ ID NO's: 6836, 6837, 7447, 8274, 8701, 9071, 9100, 9579, 10205, 10446, 10456, 10604, 10737 and 11018.

The isolated nucleic acid molecule comprising a nucleotide sequence encodes all or a portion of a protein homologue capable of conferring resistance to heavy metals, wherein the amino acid sequence of the protein homologue is substantially identical to one of the sequences as set forth in SEQ ID NO's: 7432, 7741, 8701, 8706, 8828, 8829, 9071, 9181, 9271, 10600 and 11018. Those genes may be introduced into crop plants to provide for resistance to a heavy metal in a poor growing conditions (U.S. Pat. No. 6,426,447). Therefore, those skilled in the art will find the utility of these nucleotide sequences in trait development in plants.

The isolated nucleic acid molecule comprising a nucleotide sequence encodes all or a portion of a RTX (repeats in toxin) homologue, the amino acid sequence of which is substantially identical to one of the sequences as set forth in SEQ ID NO's: 9946, 10551 and 10643. RTX belongs to the cytolytic toxin family. Within the medical sciences, there is growing interest in the potential utility of purified mammalian antibodies in the diagnosis and treatment of disease. For example, tagged antibodies directed against tumor cell surface antigens provide a highly sensitive and specific means for detecting and classifying various cancers. One therapeutic application using antibodies involves the administration of purified tumor-specific antibodies that are chemically coupled to cytotoxic agents. A class of cytotoxins that holds particular promise in the treatment of cancers consists of protein toxins from plants. However, progress in the treatment of cancers using chemically coupled antibodies and cytotoxins has been impeded by the lack of a cost effective means for producing these molecules in a pharmaceutically acceptable grade and in commercially acceptable quantities. Therefore, the nucleotide sequences of the invention encoding the cytotoxin homologs may be overexpressed in plants and large quantities of the cytotoxin proteins may be produced, isolated and purified from the plants. These purified toxins may be used as a therapeutic agent (U.S. Pat. No. 6,140,075).

The isolated nucleic acid molecule comprising a nucleotide sequence encodes all or a portion of a PapA protein homologue, the amino acid sequence of which is substantially identical to the sequence set forth in SEQ ID NO: 7514. PapA is shown to have cytotoxicity to larval hemocyes of an insect and, therefore, may be used as an insecticidal protein (Khandelwal et al., Biochem. Biophy. Res. Commun. 314: 943-949, 2004).

The isolated nucleic acid molecule comprising a nucleotide sequence encodes all or a portion of a pyoverdin protein homologue, the amino acid sequence of which is substantially identical to the sequence set forth in SEQ ID NO: 6598. Pyoverdin is a fluorescent siderophore secreted by *Pseudomonas aeruginosa* group. It's used to help the microbe leech iron out of its surroundings and is produced mostly in iron deficient environments. Pyoverdin competes directly with transferrin for iron and that it is an essential element for in vivo iron gathering and virulence expression in *P. aeruginosa*. It is indicated that it plays essential role in bacterial growth and development (Meyer et al., Infect Immun. 64 (2): 518-523, 1996).

The isolated nucleic acid molecule comprising a nucleotide sequence encodes all or a portion of a Zinc finger protein homologue, the amino acid sequence of which is substantially identical to the sequence as set forth in SEQ ID NO: 8011. A zinc finger is part of a protein that can bind to DNA. Zinc-finger proteins regulate the expression of genes as well as nucleic acid recognition, reverse transcription, signal transduction and virus assembly and have prominent roles in many other cellular processes. Therefore, Zinc finger proteins and their metal binding sites are promising targets for specific drug design to help ameliorate major diseases (Hanas et al., In: Zinc Finger proteins: from atomic contact to cellular function, edited by Iuchi and Kuldell, 2004).

The isolated nucleic acid molecule comprising a nucleotide sequence encodes all or a portion of an enterochelin protein homologue, the amino acid sequence of which is substantially identical to the sequence as set forth in SEQ ID NO: 8528. Enterochelin proteins are iron-binding compound of *E. coli* and *Salmonella* spp. may have utilities in antibacterial arena (Antimicrob Agents Chemother. 18 (1): 63-68, 1980).

The isolated nucleic acid molecule comprising a nucleotide sequence encodes all or a portion of a nonribosomal peptide homologue, the amino acid sequence of which is substantially identical to one of the sequences as set forth in SEQ ID NO's: 6870, 7462, 7463, 8248, 8339, 8492, 8530, 8546, 8547, 8856, 8860, 8863, 9225, 9226, 9227, 9552, 10073, 10506, 10726, 11003, 11004, 11005, 11012, 11013, 11015, 11584, 11585, 11588, 11590, 11591, 11844, 11845, 12085 and 12089.

The isolated nucleic acid molecule comprising a nucleotide sequence encodes all or a portion of a protein homologous to a protein from a *Drosophila* species the amino acid sequence of which is substantially identical to the sequence as set forth in SEQ ID NO: 7909. The gene encoding a protein homologous to a protein from *Drosophila* may affect pathogenesis in insects.

The present invention also relates to a class of isolated nucleic acid molecules comprising promoter sequences or regulatory elements, particularly those found within SEQ ID NO:12217 through SEQ ID NO:14867 or complements thereof. Particularly, the promoter sequence comprises a nucleotide sequence, wherein: (1) the nucleotide sequence hybridized under stringent conditions to a nucleotide sequence of a second isolated nucleic acid molecule selected from the group consisting of SEQ ID NO:12217 through SEQ ID NO:14867 or complements thereof; (2) the nucleotide sequence is a portion of any sequence selected from the group consisting of SEQ ID NO:12217 through SEQ ID NO:14867; or (3) the nucleotide sequence is the complement of (1) or (2). As used herein, the term "promoter" or "promoter sequence" means a nucleotide sequence that is capable of, when located in cis to a structural nucleotide sequence encoding a polypeptide or protein, functioning in a way that directs expression of one or more mRNA molecules that encodes the polypeptide or protein. Such promoter regions are typically found upstream of the trinucleotide, ATG, at the start site of a polypeptide-coding region. Promoter molecules can also include DNA sequences from which transcription of tRNA or rRNA sequences are initiated.

The present invention also relates to an isolated nucleic acid molecule comprising terminator sequences, particularly those found within SEQ ID NO:14868 through SEQ ID NO:16342 or complements thereof and refers to a nucleotide sequence that is required for the termination reaction of the transcription process. Termination involves recognition of the point at which no further bases should be added to a growing RNA chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA.

The present invention also relates to an isolated nucleic acid molecule that encodes ribosomal RNA (rRNA), transfer RNA (tRNA) molecules. Particularly, the isolated nucleic acid molecule comprise a nucleotide sequence, wherein: (1) the nucleotide sequence hybridized under stringent conditions to a nucleotide sequence of a second isolated nucleic acid molecule selected from the group consisting of SEQ ID NO:16343 through SEQ ID NO:16424 or complements thereof; (2) the nucleotide sequence is a portion of any sequence selected from the group consisting of SEQ ID NO:16343 through SEQ ID NO:16424; or (3) the nucleotide sequence is the complement of (1) or (2).

The isolated nucleic acid molecules of the present invention also include those comprising a substantial portion of a nucleotide sequence selected from the group consisting of SEQ ID NO:1 through SEQ ID NO:6108 or complements thereof. A "substantial portion" of a nucleotide sequence comprises enough of the sequence to afford specific identification and/or isolation of a nucleic acid fragment comprising the sequence. In general, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. The skilled artisan, having the benefit of the sequences as reported herein, may now use all or a substantial portion of the disclosed sequences for purposes known to him or her in this art. Accordingly, the present invention comprises the complete sequences as reported in the accompanying Sequence Listing, as well as substantial portions of those sequences as defined above.

The nucleic acids of the present invention may be used to isolate nucleic acids encoding homologous proteins from the same or other species, such as *Photorhabdus, Serratia, Yersinia, Salmonella, E. coli,* and *Erwinia* sp. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding homologous proteins, either as cDNA's or genomic DNA's, could be isolated directly by using all or a portion of the nucleic acids of the present invention as DNA hybridization probes to screen cDNA or genomic libraries from any desired organism employing methodology well known to those skilled in the art. Methods for forming such libraries are well known in the art (Sambrook et al., Molecular Cloning: A Laboratory Manual; Cold Spring Harbor Laboratory Press, Cold Spring Harbor, 1989). Specific oligonucleotide probes based upon the nucleic acids of the present invention can be designed and synthesized by methods known in the art. Moreover, the entire sequences of the nucleic acids can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full-length cDNA or genomic DNAs under conditions of appropriate stringency. Two short segments of the nucleic acids of the present invention may also be used in polymerase chain reaction protocols, for example, the RACE protocol (Frohman et al., Proc. Natl. Acad. Sci. USA 85:8998, 1988), to amplify longer nucleic acids encoding homologous genes from DNA or RNA from other sources.

Nucleic acids of interest may also be synthesized, either completely or in part, especially where it is desirable to provide plant-preferred sequences, by well-known techniques as described in the technical literature. See, e.g., Carruthers et al. (Cold Spring Harbor Symp. Quant. Biol. 47:411-418, 1982) and Adams et al. (J. Am. Chem. Soc. 105:661, 1983). Thus, all or a portion of the nucleic acids of the present invention may be synthesized using codons preferred by a selected plant host. Plant-preferred codons may be determined, for example, from the codons used in the proteins expressed in a particular plant host species (Brown et al., U.S. Pat. No. 5,689,052). Other modifications of the gene sequences may result in mutants having slightly altered activity.

Availability of the nucleotide sequences encoding *Xenorhabdus* proteins facilitates immunological screening of DNA expression libraries. Synthetic polypeptides representing portions of the amino acid sequences of *Xenorhabdus* proteins may be synthesized. These polypeptides can be used to immunize animals to produce polyclonal or monoclonal antibodies with specificity for polypeptides or proteins comprising the amino acid sequences. These antibodies can be then be used to screen expression libraries to isolate genes of interest (Lerner, Adv. Immunol 36: 1, 1984). It is understood that those skilled in the art are familiar with the standard resource materials that describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y., 1988).

The present invention relates to a method for obtaining a nucleic acid from a cell other than a *Xenorhabdus* Xs86068 cell comprising a nucleotide sequence encoding a *Xenorhabdus* protein homologue the amino acid sequence of which is at least 70% identical to a member selected from the group consisting of SEQ ID NO:6109 to SEQ ID NO:12216. In a preferred embodiment, the method of the present invention for obtaining a nucleic acid encoding all or a substantial portion of the amino acid sequence of a *Xenorhabdus* protein homologue comprising: (a) probing an expression library with a hybridization probe comprising a nucleotide sequence encoding a polypeptide having an amino acid sequence set forth in any of SEQ ID NO:6109 to SEQ ID NO:12216, or an amino acid sequence set forth in any of SEQ ID NO:6109 to SEQ ID NO:12216 with conservative amino acid substitutions; (b) identifying a DNA clone that hybridizes to the hybridization probe; (c) isolating the DNA clone identified in step (b); and (d) sequencing the DNA fragment that comprises the clone isolated in step (c) wherein the sequenced nucleic acid molecule encodes all or a substantial portion of the amino acid sequence of the *Xenorhabdus* protein homologue.

In another preferred embodiment, the method of the present invention for obtaining a nucleic acid molecule from a cell other than a *Xenorhabdus* Xs86068 cell that encodes a substantial portion of an amino acid sequence of a *Xenorhabdus* protein homologue comprising: (a) synthesizing a first and a second oligonucleotide primers corresponding to a portion of the coding sequence of a second nucleic acid molecule set forth in SEQ ID NO:1 through SEQ ID NO:6108; and (b) amplifying a DNA insert present in a cloning vector using the first and second oligonucleotide primers of step (a) wherein the amplified nucleic acid molecule encodes all or a substantial portion of the amino acid sequence of the *Xenorhabdus* protein homologue.

The present invention, in another aspect, provides a substantially purified protein or polypeptide molecule comprising an amino acid sequence, wherein the amino acid sequence is defined as follows: (1) the amino acid sequence is encoded by a nucleotide sequence that is at least 50% identical to all or a substantial portion of a coding sequence located within SEQ ID NO:1 through SEQ ID NO:6108; or (2) the amino acid sequence is substantially identical to a member selected from the group consisting of SEQ ID NO:6109 to SEQ ID NO:12216. In alternative embodiments, the nucleotide sequence is at least 55% identical, at least 60% identical, at least 65% identical, at least 70% identical, at least 75% identical, at least 80% identical, at least 85% identical, at least 90% identical, at least 95% identical to all or a substantial portion of a coding sequence located within SEQ ID NO:1 through SEQ ID NO:6108. In a further embodiment, the nucleotide sequence is 100% identical to all or a substantial portion of a coding sequence located within SEQ ID NO:1 through SEQ ID NO:6108. In a still further embodiment, the amino acid sequence is at least 60% identical, at least 70% identical, at least 80% identical, at least 90% identical, at least 95% identical to a member selected from the group consisting of SEQ ID NO:6109 to SEQ ID NO:12216.

The term "substantially purified protein or polypeptide molecule" refers to a protein sequence molecule separated from substantially all other molecules normally associated with it in its native state. More preferably a substantially purified protein sequence molecule is the predominant species present in a preparation. A substantially purified molecule may be greater than 60% free, preferably 75% free, more preferably 80% free, more preferably 90% free, and most preferably 95% free from the other molecules (exclusive of solvent) present in the natural mixture.

It is well known in the art that proteins or polypeptides may undergo modifications, including post-translational modifications, such as, but not limited to, disulfide bond formation, glycosylation, phosphorylation, or oligomerization. Thus, as used herein, the term "protein molecule" or "polypeptide molecule" includes any protein molecule that is modified by any biological or non-biological process. The terms "amino acid" and "amino acids" refer to all naturally occurring amino acids. This definition is meant to include norleucine, ornithine, homocysteine, and homoserine.

The polypeptides or proteins of the present invention may be produced via chemical synthesis, or more preferably, by expression in a suitable bacterial or eukaryotic host. Suitable methods for expression of the polypeptides or proteins are described by Sambrook et al. (ibid). The polypeptides or protein molecules of the present invention may also include fusion protein sequence molecules. A protein sequence molecule that comprises one or more additional polypeptide regions not derived from that protein molecule is a "fusion" protein sequence molecule. Such molecules may be derivatized to contain carbohydrate or other moieties (such as keyhole limpet hemocyanin, etc.). Fusion protein sequence molecules of the present invention are preferably produced via recombinant means.

Another aspect of the present invention concerns antibodies, single-chain antigen binding molecules, or other proteins that specifically bind to one or more of the protein sequence molecules of the present invention and their homologues, fusions or fragments. Such antibodies may be used to quantitatively or qualitatively detect the protein sequence molecules of the present invention. As used herein, an antibody or polypeptide is said to "specifically bind" to a protein sequence molecule of the present invention if such binding is not competitively inhibited by the presence of non-related molecules. For example, the antibodies of the present invention bind to protein sequence molecules of the present invention, in a more preferred embodiment, the antibodies of the present invention bind to protein sequence molecules derived from Xenorhabdus that comprise SEQ ID NO:6109 through SEQ ID NO:12216.

Nucleic acid molecules that encode all or part of the protein sequence of the present invention can be expressed, via recombinant means, to yield protein or polypeptides that can in turn be used to elicit antibodies that are capable of binding the expressed protein or polypeptide. Such antibodies may be used in immunoassays for that protein or polypeptide. Such protein or polypeptide-encoding molecules, or their fragments may be "fusion" molecules (i.e., a part of a larger nucleic acid molecule) such that, upon expression, a fusion protein is produced. It may be desirable to derivatize the obtained antibodies, for example, with a ligand group (such as biotin) or a detectable marker group (such as a fluorescent group, a radioisotope or an enzyme). Such antibodies may be used in immunoassays for that protein or may be used to screen DNA expression libraries to isolate clones containing full-length insert of genes (Lerner, Adv. Immunol. 36: 1, 1984).

In one embodiment, the antibodies of the present invention specifically bind to one or more of the insect inhibitory polypeptides or proteins of the present invention comprising SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693. Such antibodies may be used to detect the presence of such insect inhibitory polypeptides or proteins in a sample.

The present invention also provides a method for detecting an insect inhibitory polypeptide or protein in a biological sample, wherein the method comprises the steps of: (1) obtaining a biological sample; (2) contacting the sample with an antibody that specifically binds to the polypeptide or protein comprising SEQ ID NO: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 or 11693, under conditions effective to allow the formation of complexes; and (3) detecting the complexes so formed.

The present invention also relates to a plant recombinant vector or construct comprising a structural nucleotide sequence encoding a Xenorhabdus protein sequence comprising an amino acid sequence that is selected from the group consisting of SEQ ID NO:6108 through SEQ ID NO:12216. In one embodiment, a plant recombinant vector or construct of the present invention comprises a structural nucleotide sequence encoding an insect inhibitory protein sequence of the present invention comprising an amino acid sequence that is selected from the group consisting of SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693. The present invention also relates to a transformed plant cell or plant comprising in its genome an exogenous nucleic acid encoding one or more Xenorhabdus proteins or polypeptides of the present invention. The present invention also relates to methods for creating a transgenic plant in which one or more Xenorhabdus proteins or polypeptides of the present invention are overexpressed.

As used herein, "structural nucleotide sequence" refers to a nucleotide sequence that is expressed to produce a polypeptide. The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

Methods that are well known to those skilled in the art may be used to construct the plant recombinant construct or vector of the present invention. These methods include in vitro recombinant DNA techniques, synthetic techniques, and in vivo genetic recombination. Such techniques are described in Sambrook et al. (ibid); and Ausubel et al. (Current Protocols in Mol. Biol., John, Wiley & Sons, New York, N.Y., 1989).

A plant recombinant construct or vector of the present invention contains a structural nucleotide sequence encoding one or more Xenorhabdus proteins or polypeptides of the present invention as set forth in SEQ ID NO:6109 through SEQ ID NO:12216 and operably linked regulatory sequences or control elements.

The term "operably linked", as used in reference to a regulatory sequence and a structural nucleotide sequence, means that the regulatory sequence causes regulated expression of the operably linked structural nucleotide sequence.

"Regulatory sequences" or "control elements" refer to nucleotide sequences located upstream (5' noncoding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

It is understood by those skilled in the art that different promoters may direct the expression of a gene in different tissues or cell types, or at different stages of development, or in response to different environmental conditions. For example, promoters that may be used in the present invention include, but are not limited to, constitutive promoters [e.g., the nopaline synthase (NOS) promoters (Ellis et al., EMBO Journal 6:11-16, 1987); the cauliflower mosaic virus (CaMV) 35S (Fraley et al., U.S. Pat. No. 5,858,742); and actin promoters, such as the *Arabidopsis* actin gene promoter (see, e.g., Huang, Plant Mol. Biol. 33:125-139, 1997)], inducible promoter [e.g., the drought-inducible promoter of maize (Busk, Plant J. 11:1285-1295, 1997; the cold, drought, and high salt inducible promoter from potato (Kirch, Plant Mol. Biol. 33:897-909, 1997; and salicylic acid inducible promoter (Uknes et al., Plant Cell 5:159-169, 1993)] and tissue-specific promoters [e.g., leaf-specific promoters [e.g., Matsuoka, Plant J. 6:311-319, 1994; Shiina, Plant Physiol. 115-477-483, 1997); root-specific promoters (e.g., Samac et al., *Plant Mol. Biol.* 25: 587-596, 1994; Yamamoto, Plant Cell 3:371-382, 1991), tuber-specific promoters (Hannapel, *Plant Physiol.* 101: 703-704, 1993; Bevan et al., *EMBO J.* 8: 1899-1906, 1986), seed-specific promoters (e.g., Sheridan, Genetics 142:1009-1020, 1996; Abler, Plant Mol. Biol. 22:10131-1038, 1993) and pollen-specific promoter (e.g., Guerrero, Mol. Gen. Genet. 224: 161-168, 1990; Wakeley, Plant Mol. Biol. 37:187-192, 1992).

It is recognized that additional promoters that may be utilized are described, for example, in U.S. Pat. Nos. 5,378, 619, 5,391,725, 5,428,147, 5,447,858, 5,608,144, 5,608,144, 5,614,399, 5,633,441, 5,633,435, and 4,633,436. In addition, a tissue specific enhancer may be used (Fromm et al., *The Plant Cell* 1:977-984, 1989). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, and plant rubisco leaders, among others (Turner and Foster, Molecular Biotechnology 3:225, 1995).

The 3' non-translated sequence or 3' transcription termination region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., Proc. Natl. Acad. Sci. USA, 80: 4803-4807, 1983). The use of different 3' nontranslated regions is exemplified by Ingelbrecht et al. (Plant Cell 1:671-680, 1989).

A recombinant vector or construct of the present invention will typically comprise a selectable marker that confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183-188, 1985) which codes for kanamycin resistance and can be selected for using kanamycin, G418, etc.; a mutant EPSP synthase gene (Hinchee et al., *Bio/Technology* 6:915-922, 1988) which encodes glyphosate resistance; and a nitrilase gene which confers resistance to bromoxynil (Stalker et al., *J. Biol. Chem.* 263:6310-6314, 1988).

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405, 1987; Jefferson et al., *EMBO J.* 6:3901-3907, 1987); an R-locus gene (Dellaporta et al., Stadler Symposium 11:263-282, 1988); a β-lactamase gene (Sutcliffe et al., *Proc. Natl. Acad. Sci.* (*U.S.A.*) 75:3737-3741, 1978); and a luciferase gene (Ow et al., *Science* 234:856-859, 1986). Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In preparing the DNA constructs of the present invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The present invention also provide a transgenic plant comprising in its genome an isolated nucleic acid which comprises: (1) a 5' non-coding sequence which functions in the cell to cause the production of a mRNA molecule; which is linked to (2) a structural nucleotide sequence, wherein the structural nucleotide sequence encodes a *Xenorhabdus* protein sequence of the present invention that is substantially identical to a member selected from the group consisting of SEQ ID NO:6109 to SEQ ID NO:12216; which is linked to (3) a 3' non-translated sequence that functions in said cell to cause termination of transcription.

The term "transgenic plant" refers to a plant that contains an exogenous nucleic acid, which can be derived from the same plant species or from a different plant species. Transgenic plants of the present invention preferably have incorporated into their genome or transformed into their chloroplast or plastid genomes a selected polynucleotide (or "transgene"), that comprises at least a structural nucleotide sequence that encodes a polypeptide the amino acid sequence of which is selected from the group consisting of SEQ ID NO:6109 to SEQ ID NO:12216 or, in particular, an insect inhibitory polypeptide the amino acid sequence of which is selected from the group consisting of SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693. Transgenic plants are also meant to comprise progeny (decendant, offspring, etc.) of any generation of such a transgenic plant. A seed of any generation of all such transgenic insect-resistant plants wherein said seed comprises a DNA sequence encoding the polypeptide of the present invention is also an important aspect of the invention.

The DNA constructs of the present invention may be introduced into the genome of a desired plant host by a variety of conventional transformation techniques, which are well known to those skilled in the art. Preferred methods of transformation of plant cells or tissues are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al. (Nature 303:209, 1983); Bevan (Nucleic Acids Res. 12: 8711-8721, 1984); Klee et al. (Bio-Technology 3(7): 637-642, 1985); and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a nucleic acid encoding a polypeptide or protein of the present invention in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., Proc. Natl. Acad. Sci. USA 80: 4803-4807, 1983). This expression cassette may be assembled on high copy replicons suitable for the production of large quantities of DNA.

When adequate numbers of cells (or protoplasts) containing the exogenous nucleic acid encoding a polypeptide or protein of the present invention are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al. (Handbook of Plant Cell Culture—Crop Species. Macmillan Publ. Co., 1984); Shimamoto et al (Nature 338:274-276, 1989); Vasil et al. (Bio/Technology 8:429-434, 1990; Bio/Technology 10:667-674, 1992); Hayashimoto (Plant Physiol. 93:857-863, 1990); and Datta et al. (Bio-technology 8:736-740, 1990). Regeneration can also be obtained from plant callus, explants, organs, or parts thereof. Such regeneration techniques are described generally in Klee et al. (Ann. Rev. Plant Phys. 38:467-486, 1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seeds produced and analyzing the resulting plants produced for the exogenous gene of interest.

The development or regeneration of transgenic plants containing the exogenous nucleic acid that encodes a polypeptide or protein of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide or protein of the present invention is cultivated using methods well known to one skilled in the art.

Transgenic plants, that can be generated by practice of the present invention, include but are not limited to Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The present invention also provides parts of the transgenic plants of present invention. Plant parts, without limitation, include seed, endosperm, ovule and pollen. In a particularly preferred embodiment of the present invention, the plant part is a seed.

The present invention also further provides method for generating a transgenic plant comprising the steps of: a) introducing into the genome of the plant an exogenous nucleic acid, wherein the exogenous nucleic acid comprises in the 5' to 3' direction i) a promoter that functions in the cells of said plant, said promoter operably linked to; ii) a structural nucleic acid sequence encoding a polypeptide or protein of the present invention that is selected from the group consisting of SEQ ID NO:6109 to SEQ ID NO:12216 or, in particular, an insect inhibitory polypeptide that is selected from the group consisting of SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693, said structural nucleic acid sequence operably linked to; iii) a 3' non-translated nucleic acid sequence that functions in said cells of said plant to cause transcriptional termination; b) obtaining transformed plant cells containing the nucleic acid sequence of step (a); and c) regenerating from said transformed plant cells a transformed plant in which said polypeptide or protein is overexpressed.

Any of the isolated nucleic acid molecules of the present invention may be introduced into a plant cell in a permanent or transient manner in combination with other genetic elements such as vectors, promoters, enhancers etc. Further any of the nucleic acid molecules encoding a Xenorhabdus protein sequence of the present invention may be introduced into a plant cell in a manner that allows for over expression of the protein sequence encoded by the nucleic acid molecule.

The nucleotide sequences of the present invention may be introduced into a wide variety of prokaryotic and eukaryotic microorganism hosts to express the Xenorhabdus polypeptide or protein of the present invention, particularly the insect inhibitory polypeptides or proteins of the present invention comprising an amino acid sequence that is selected from the group consisting of SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693. The term "microorganism" includes prokaryotic and eukaryotic microbial species such as bacteria and fungi. Illustrative prokaryotes, whether Gram-negative, Gram-positive, or otherwise, include Enterobacteriaceae, such as *Escherichia, Erwinia, Shigella, Salmonella*, and *Proteus*; Bacillaceae, Rhizobiceae, such as *Rhizobium*; Spirillaceae, such as photobacterium, *Zymomonas, Serratia, Aeromonas, Vibrio, Desulfovibrio, Spirillum*, Lactobacillaceae; Pseudomonadaceae, such as *Pseudomonas* and *Acetobacter*; Azotobacteraceae, Actinomycetales, and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

For the purpose of plant protection against insects, a large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed recombinant constructs. These microorganisms include bacteria, algae, and fungi. Of particular interest are microorganisms, such as bacteria, e.g., genera *Bacillus* (including the species and subspecies); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*.

The present invention also relates to a bacterial or a fungal recombinant construct. The recombinant construct may comprise a structural nucleotide sequence encoding a Xenorhabdus protein sequence comprising an amino acid sequence that is selected from the group consisting of SEQ ID NO:6109 to SEQ ID NO:12216. The present invention also relates to methods for obtaining a recombinant bacterial or fungal host cell, comprising introducing into a bacterial or fungal host cell an exogenous nucleic acid molecule that is selected from the group consisting of SEQ ID NO:1 to SEQ ID NO:6108.

The recombinant construct for producing a polypeptide in a bacterium also contains an inducible promoter that is recognized by the host bacterium and is operably linked to the nucleic acid encoding, for example, the nucleic acid molecule encoding the Xenorhabdus protein sequence of interest. Inducible promoters suitable for use with bacterial hosts include the β-lactamase, *E. coli* λ phage $P_L$ and $P_R$, and *E. coli* galactose, arabinose, alkaline phosphatase, tryptophan (trp), and lactose operon promoter systems and variations thereof (Chang et al., *Nature* 275:615, 1978; Goeddel et al., *Nature* 281:544, 1979; Guzman et al., *J.*

Bacteriol. 174:7716-7728, 1992; Goeddel, *Nucleic Acids Res.* 8:4057, 1980; EP 36,776). Hybrid promoters such as the tac promoter (deBoer et al., *Proc. Natl. Acad. Sci.* (*USA*) 80:21-25, 1983) and other known bacterial inducible promoters are suitable (Siebenlist et al., *Cell* 20:269, 1980) may also be used.

The bacterial recombinant construct or vector may be a linear or a closed circular plasmid. The vector system may be a single vector or plasmid or two or more vectors or plasmids that together contain the total DNA to be introduced into the genome of the bacterial host. In addition, the bacterial vector may be an expression vector. Nucleic acid molecules encoding *Xenorhabdus* proteins or polypeptide can, for example, be suitably inserted into a replicable vector for expression in a bacterium under the control of a suitable promoter for that bacterium. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, a promoter allowing the expression of an exogenous nucleotide sequence and a structural nucleotide sequence of the present invention.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2:95, 1977). The pBR322 plasmid contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes. In addition, nucleic acid molecules encoding *Xenorhabdus* proteins or polypeptides may be expressed not only directly, but also as a fusion with another polypeptide, preferably a signal sequence or other polypeptide having a specific cleavage site at the N-terminus of the mature polypeptide. The suitable vectors containing one or more of the above-listed components may be constructed employing standard recombinant DNA techniques. Isolated plasmids or DNA fragments are cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, a *Xenorhabdus* protein sequence of the present invention, may be ligated into the vector in frame with sequences for the amino-terminal Met and the subsequent 7 residues of β-galactosidase so that a hybrid protein is produced; pIN vectors (Van Heeke and Schuster *J. Biol. Chem.* 264:5503-5509, 1989); and the like. pGEX vectors (Promega, Madison, Wis.) may also be used to express foreign polypeptides as fusion proteins with glutathione S-transferase (GST). Bacterial cells used to produce the polypeptide of interest for purposes of this invention are cultured in suitable media in which the promoters for the nucleic acid encoding the heterologous polypeptide can be artificially induced as described generally, e.g., in Sambrook et al., ibid). Examples of suitable media are given in U.S. Pat. Nos. 5,304,472 and 5,342,763.

A yeast recombinant construct can typically include one or more of the following: a promoter sequence, a fusion partner sequence, a leader sequence, a transcription termination sequence and a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., Gene, 8:17-24, 1979), pCl/1 (Brake et al., Proc. Natl. Acad. Sci. USA, 81:4642-4646, 1984), and YRp17 (Stinchcomb et al., J. Mol. Biol., 158:157, 1982).

The nucleotide sequence provided in one of SEQ ID NO:1 through SEQ ID NO:6108 or a fragment thereof, or a complement thereof, or a nucleotide sequence at least about 70% identical, preferably about 80% or about 90% identical, even more preferably about 95%, about 98% or 100% identical to the nucleotide sequence provided in one of SEQ ID NO:1 through SEQ ID NO:6108 or a fragment thereof, or a complement thereof, can be "provided" in a variety of media to facilitate its use. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410, 1990) and BLAZE (Brutlag et al., *Comp. Chem.* 17:203-207, 1993) search algorithms on a Sybase system can be used to identify open reading frames (ORFs) within the genome that contain homology to ORFs or proteins from other organisms. Such ORFs are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

Nucleic acid molecules and fragments thereof of the present invention may be employed to obtain other nucleic acid molecules from the same or closely related species. Such nucleic acid molecules include the nucleic acid molecules that encode the complete coding sequence of a protein, and promoters, and flanking sequences of such molecules. In addition, such nucleic acid molecules include nucleic acid molecules that encode for other isozymes or gene family members. Such molecules can be readily obtained by using the above-described nucleic acid molecules or fragments thereof to screen genomic libraries obtained from *Xenorhabdus*. Methods for forming such libraries are well known in the art.

Nucleic acid molecules and fragments thereof of the present invention may also be employed to obtain other nucleic acid molecules such as nucleic acid homologues. Such homologues include the nucleic acid homologues of non-*Xenorhabdus* species including the nucleic acid molecules that encode, in whole or in part, protein homologues of other species or other organisms, sequences of genetic elements such as promoters and transcriptional regulatory elements. Such molecules can be readily obtained by using the above-described nucleic acid molecules or fragments thereof to screen cDNA or genomic libraries. Methods for forming such libraries are well known in the art. Such homologue molecules may differ in their nucleotide sequences from those found in one or more of SEQ ID NO:1 through SEQ ID NO:6108 or complements thereof because complete complementarity is not needed for stable hybridization. The nucleic acid molecules of the present invention therefore also include molecules that, although capable of specifically hybridizing with the nucleic acid molecules, may lack "complete complementarity." In a particular embodiment, methods for obtaining these molecules may be used [Frohman, M. A. et al., *Proc. Natl. Acad. Sci.* (*U.S.A*) 85:8998-9002, 1988; Ohara, O. et al., *Proc. Natl. Acad. Sci.* (*U.S.A.*) 86:5673-5677, 1989].

The nucleic acid molecules of the present invention may be used for physical mapping. Physical mapping, in conjunction with linkage analysis, can enable the isolation of genes. Physical mapping has been reported to identify the markers closest in terms of genetic recombination to a gene target for cloning. Once a DNA marker is linked to a gene of interest, the chromosome walking technique can be used to find the genes via overlapping clones. For chromosome walking, random molecular markers or established molecular linkage maps are used to conduct a search to localize the gene adjacent to one or more markers. A chromosome walk (Bukanov and Berg, *Mo. Microbiol.* 11:509-523, 1994; Birkenbihl and Vielmetter *Nucleic Acids Res.* 17.5057-5069, 1989; Wenzel and Herrmann, *Nucleic Acids Res.* 16:8323-8336, 1988) is then initiated from the closest linked marker. Starting from the selected clones, labeled probes specific for the ends of the insert DNA are synthesized and used as probes in hybridizations against a representative library. Clones hybridizing with one of the probes are picked and serve as templates for the synthesis of new probes; by subsequent analysis, contigs are produced. The degree of overlap of the hybridizing clones used to produce a contig can be determined by comparative restriction analysis. The most frequently used procedures are, fingerprinting (Coulson et al, *Proc. Natl. Acad. Sci.* (*U.S.A.*) 83:7821-7821, 1986; Knott et al., *Nucleic Acids Res.* 16:2601-2612, 1988; Eiglmeier et al., *Mol. Microbiol.* 7:197-206, 1993), restriction fragment mapping (Smith and Birnstiel, Nucleic Acids Res. 3:2387-2398, 1976), or the "landmarking" technique (Charlebois et al. *J. Mol. Biol.* 222:509-524, 1991).

Nucleic acid molecules of the present invention can be used to monitor expression. A microarray-based method for high-throughput monitoring of gene expression may be utilized to measure gene-specific hybridization targets. This 'chip'-based approach involves using microarrays of nucleic acid molecules as gene-specific hybridization targets to quantitatively measure expression of the corresponding genes (Schena et al., *Science* 270:467-470, 1995; Shalon, Ph.D. Thesis, Stanford University, 1996). Every nucleotide in a large sequence can be queried at the same time. Hybridization can be used to efficiently analyze nucleotide sequences.

It is understood that one or more of the molecules of the present invention, preferably one or more of the nucleic acid molecules or protein molecules or fragments thereof of the present invention may be utilized in a microarray-based method. In one embodiment, the microarray of the present invention comprises at least 10 nucleic acid molecules, more preferably at least 100 nucleic acid molecules, and even more preferably at least 1000 nucleic acid molecules, that specifically hybridize under stringent conditions to at least 10, at least 100, at least 1000, nucleic acid molecules, respectively, encoding *Xenorhabdus* proteins or polypeptides or fragments thereof set forth in SEQ ID NO:1 through SEQ ID NO:6108 or fragment thereof or complement. In a further embodiment, the microarray of the present invention comprises at least 2,500 nucleic acid molecules that specifically hybridize under stringent conditions to at least 2,500 nucleic acid molecules that encode a *Xenorhabdus* protein sequence or fragment thereof set forth in SEQ ID NO:6109 through SEQ ID NO: 12216. While it is understood that a single nucleic acid molecule may encode more than one protein homologue or fragment thereof, in a preferred embodiment, at least 50%, preferably at least 70%, more preferably at least 80%, even more preferably at least 90% of the nucleic acid molecules that comprise the microarray contain one protein or fragment thereof.

Nucleic acid molecules of the present invention may be used in site directed mutagenesis. Site-directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site-directed mutagenesis are often employed and these are cassette mutagenesis (Wells et al., *Gene* 34:315-23, 1985), primer extension [Gilliam et al., *Gene* 12:129-137, 1980; Zoller and Smith, *Methods Enzymol.* 100:468-500, 1983; and Dalbadie-McFarland et al., *Proc. Natl. Acad. Sci.* (*U.S.A.*) 79:6409-6413, 1982] and methods based upon PCR (Scharf et al., *Science* 233:1076-1078, 1986); Higuchi et al., *Nucleic Acids Res.* 16:7351-7367, 1988). Site-directed mutagenesis approaches are also described in US Patent Pub. No. 20020151072, European Patent 0 385 962, European Patent 0 359 472, and PCT Patent Application WO 93/07278. Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., ibid).

Insect inhibitory protein-encoding nucleic acids of the present invention will find particular uses in the plant protection against insects. For instance, insect-resistant transgenic plants can be generated by introducing the exogenous nucleic acids encoding an insect inhibitory polypeptide or protein or insect inhibitory fragment thereof, the amino acid sequence of which is substantially identical to a sequence set forth in SEQ ID NO's: 6903, 6904, 6905, 7110, 7179, 7514, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693. The methods for generating such insect-resistant transgenic plants have been disclosed herein.

Insect inhibitory protein-encoding nucleic acids of the present invention will also find particular uses in engineering a transgenic microorganism (bacteria or fungi) to express the insect inhibitory polypeptides or proteins of the present invention and then to apply them to the insect food source or allow them to reside in soil surrounding plant roots or on the surface of plant leaves. The transgenic microorganisms of the present invention may be used to produce *Xenorhabdus* polypeptides or proteins of interest, particularly insect inhibitory polypeptides or proteins. Insect inhibitory polypeptides or proteins or insect inhibitory fragments thereof may be secreted, for example as in bacterial systems, meaning targeted to either the periplasm as for gram negative bacteria or localized to the extracellular space for gram negative or any other type of bacterium, or localized to the intracellular spaces within the cytoplasm. Such compositions may be administered to insects according to methods well known in the art.

Insecticidal proteins of the present invention can be used together with other insecticidal or pesticidal agents, such as organic chemical compositions, organo-phosphate compositions, nerve agents, diverse insecticidal proteins such as Bt cry, vip, TIC, and EG related insecticidal proteins, as well as with agents designed for dsRNA mediated gene suppression.

The principle object of the present invention is to provide a method for identification of any gene or any protein encoded by any structural gene contained within a *Xenorhabdus* species, particularly those species which are shown to exhibit the production of an insect inhibitory protein or molecule or other similarly active composition, either alone or in combination with proteins or molecules or other similarly active compositions which may be derived from the bacterium in its role as a natural symbiont within an insect pathogenic nematode host. Isolation and identification of a single insect pathogenic nematode species enables the skilled artisan to isolate at least one species of *Xenorhabdus* endosymbiotic bacteria from the haemolymph of an insect larvae or adult which has been invaded by the isolated and identified host nematode. The isolation and purification of an insect pathogenic nematode *Xenorhabdus* symbiont bacterium from an insect cadaver provides the basis for obtaining an amount of genomic DNA from which a genomic library can be constructed to represent the entire genome of the bacterial strain. The library can then be manipulated as described herein to produce linear nucleotide sequences, which can then be compared to each other to identify regions of identity with which an overlapping sequence can be generated to produce islands of linear sequence known as contigs because of the contiguous linear sequence assembled from smaller bits of sequence data. The contigs can be assembled into a genomic map from which genes can be identified, and wherein translation of structural genes lead to further identification of proteins having predicted structure and function based on homologies of such predicted protein sequences as translated from open reading frames contained within the genome map, to proteins of known sequence, and perhaps also of known structure and function identified previously from other bacterial, viral, fungal, or other eukaryotic sources.

The *Xenorhabdus* strain Xs86068 and isolatable protein compositions exhibiting insecticidal activity as disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells that expresses a novel protein disclosed herein. In another important embodiment, the bioinsecticide composition comprises a water dispersible granule. This granule comprises bacterial cells that express a novel insecticidal protein disclosed herein. In a third important embodiment, the bioinsecticide composition comprises a wettable powder, dust, pellet, or colloidal concentrate. This powder comprises bacterial cells that express a novel insecticidal protein disclosed herein. Such dry forms of the insecticidal compositions may be formulated to dissolve immediately upon wetting, or alternatively, dissolve in a controlled-release, sustained-release, or other time-dependent manner. In a fourth important embodiment, the bioinsecticide composition comprises an aqueous suspension of bacterial cells such as those described above that express the insecticidal protein. Such aqueous suspensions may be provided as a concentrated stock solution which is diluted prior to application, or alternatively, as a diluted solution.

Exemplary bacterial cells for fulfilling the above methods may comprise *Xenorhabdus* Xs86068 cells. However, bacteria such as *Bacillus, Salmonella, Agrobacterium, Rhizobium, Erwinia, Azotobacter, Azospirillum, Klebsiella, Flavobacterium* and *Alcaligenes*, other *Xenorhabdus* or *Photorhabdus* species, or *Pseudomonas* transformed with a DNA segment disclosed herein and expressing the insecticidal protein are also contemplated to be useful.

Alternatively, the novel *Xenorhabdus* insecticidal proteins of the present invention may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate insecticidal proteins or whole cells from bacterial cultures expressing the insecticidal protein(s) of the present invention and apply solutions, suspensions, or colloidal preparations of such insecticidal proteins or whole cells as the active bioinsecticidal composition.

Regardless of the method of application, the amount of the active component(s) is applied at an insecticidally-effective amount, which will vary depending on such factors as, for example, the specific coleopteran insects to be controlled, or the specific piercing and sucking insect to be controlled, the specific plant or crop to be treated, the environmental conditions, and the method, rate, and quantity of application of the insecticidally-active composition.

The insecticide compositions described herein may be made by formulating either the bacterial cells, insecticidal protein suspensions, or isolated protein components with the desired agriculturally acceptable carrier (U.S. Pat. No. 6,177,615). The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application (U.S. Pat. Nos. 5,616,319 and 5,942,658). Suitable agricultural carriers can be solid or liquid and are well known in the art. The insecticidal compositions of this invention are applied to the environment of the target coleopteran or piercing and sucking insect, typically onto the foliage of the plant or crop to be protected, by conventional methods, preferably by spraying (U.S. Pat. No. 6,177,615). The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well known to those of skill in the art.

The insecticidal compositions may be employed in the method of the present invention singly or in combination with other compounds, including and not limited to other insecticidal proteins and pesticides. The method of the invention may also be used in conjunction with other treatments such as surfactants, detergents, polymers or time-release formulations. The insecticidal compositions of the present invention may be formulated for either systemic or topical use.

Having now generally described the invention, the same will be more readily understood through reference to the following examples that are provided by way of illustration, and are not intended to be limiting of the present invention, unless specified.

EXAMPLES

Example 1

This example illustrates the isolation of *Xenorhabdus* bacteria.

*Xenorhabdus nematophila* bacterium, strain Xs86068, was isolated from entomopathogenic nematodes according to the following procedure. Entomopathogenic nematodes were isolated from soil samples and entomopathogenic nematode suspensions were prepared according to the entomopathogenic nematode baiting method as disclosed in the US patent application (application Ser. No. 09/897,516). A variety of fourth instar insect larvae that included Western corn rootworm (WCR, *Diabrotica virgifera virgifera*), corn ear worm (CEW, *Helicoverpa zea*), tobacco bud worm (TBW, *Heliothis virescens*), black cut worm (BCW, *Agrotis epsilon*), beet army worm (BAW, *Spodoptera exigua*), boll weevil (BWV, *Anthomonas grandis grandis*), and *Galleria mellonella* were placed individually in a 24-well plate containing Whatman filters in each well. Approximately ten microliters (μL) of an entomopathogenic nematode suspension were added into each well with one insect. The plates was sealed with Parafilm™ and placed at 25° C. in the dark. After 48 to 72 hours dead insect larvae were removed from the 24-well plate. The insect larvae were surface sterilized [20 milliliter (mL) $H_2O$, 3 mL 4M NaOH and 1 mL 5% NaOCl) for 5 minutes and air-dried. The insect larvae were cut open with sterile instruments on the lateral side without injuring the gut and the hemolymph was streaked on indicator plates (NBTA and NA). The agar plates were incubated at 30° C. in the dark for 48 hours.

Characteristic blue colonies were selected from the indicator plates: phase I *Xenorhabdus* bacteria were able to take up bromthymol blue dye from the NBT agar and form the blue colonies. Bacterial characterization was performed according to methods known to the one skilled in the art (Farmer, *Bergey's Manual of Systematic Bacteriology*, Vol. 1: 510-511, 1984; Akhurst & Boemare, *J. Gen. Microbiol.*, Vol. 133: 1835-1845, 1988; Boemare et al., *Int. J. Syst. Bacteriol.*, Vol. 44: 249-255, 1993).

Single characteristic phase I colonies were picked up by an inoculation loop and suspended into BHI media (Brain Heart Infusion medium (Difco), 32 g/l, 50 mL in a 250 mL baffled flask). The bacteria were grown at 25° C. at 280 rpm on a rotary shaker in the dark. After 24 hours 15% glycerol was added to the bacterial culture, 1.5 mL aliquots for stock cultures were placed into cryovials and stored at −80° C.

The isolated *Xenorhabdus* strain Xs86068 was deposited according to the Budapest Treaty on the International Recognition of the Deposit of Microorganisms for the Purpose of Patent Procedures with the Agriculture Research Culture Collection (NRRL) International Depositary Authority at 1815 North University Street, in Peoria, Ill., ZIP 61604, U.S.A., on Jul. 26, 2004 and designated as NRRL B-30757. It is contemplated for use as a source for DNA sequences encoding insecticidal and other types of useful proteins, and when formulated into a composition of matter as a spray, powder or emulsion, for the treatment of plants or animals to inhibit insect infestation and the like.

Example 2

This example illustrates the construction and characterization of a *Xenorhabdus* genomic library.

Genomic DNA from *Xenorhabdus*, strain Xs86068, was prepared for construction of a genomic library using methods well known in the art. Xs86068 bacterial cells were grown in brain heart infusion broth (Difco) for 42 hours at 25° C. to mid-exponential phase (OD650 approximately 1.0). Cells were poured into ten 1.5 mL-microcentrifuge tubes and spun for 5 minutes at about 10,000 RPM to pellet. The supernatant was removed and the cells were frozen. The frozen pellets were resuspended into 200 µL of TE (10 mM Tris, 1 mM EDTA, pH 8.0). Genomic DNA was prepared from the frozen cell pellets using the Promega Genomic Preparation kit following the instructions of the manufacturer (Promega Corp., Madison, Wis.). Ten DNA samples were prepared from the cells above, and two of the samples were resuspended into 50 µL of TE. Sample purity was tested and confirmed by digestion using the restriction enzymes EcoRI, HindIII, NotI, and SalI. The resuspended samples were used for the preparation of the genomic library.

The genomic library of *Xenorhabdus* strain Xs86068, LIB4695, was prepared according to standard procedures well known to those skilled in the art. Genomic DNA was sheared and then polished with T4 polymerase and T4 polynucleotide kinase. LIB4695 was constructed from fragments 2-5 KB in length. Size fractionated fragments were recovered from an agarose gel. Blunt end ligation was used to clone DNA fractions into the HincII site of the standard cloning vector pUC18. The resulting ligation reactions were transformed into *E. coli* DH10B. The resulting vector fragment contains an intact beta-lactamase coding sequence enabling selection of transformed cells containing genomic DNA insertions on media containing ampicillin. Ninety-six ampicillin resistant transformants were inoculated into 96 well deep well boxes containing TB media and ampicillin to determine the efficiency of the library construction. 95% of colonies arising from the transformation contained an insert, presumably derived from the genomic sequences. Approximately 15,000 colony-forming units per microliter of ligation mix were obtained. About thirty thousand individual recombinant colonies from each library were selected for DNA sequence analysis of inserted genomic DNA.

Example 3

This example serves to illustrate the generation and assembly of *Xenorhabdus* genome sequences and the assembly into contiguous sequences. The two basic methods for the DNA sequencing are the chain termination method of Sanger et al., *Proc. Natl. Acad. Sci. (U.S.A.)* 74:5463-5467, 1977) and the chemical degradation method of Maxam and Gilbert, *Proc. Natl. Acad. Sci. (U.S.A.)* 74:560-564, 1977). PHRED (phragment editor, Phil Green, University of Washington) was used to call the bases from the sequence trace files and to assign quality scores to the bases. After the base calling was completed, sequence preprocessing was performed by removing 5' and 3' vector and linker sequences, according to standard procedures well known in the art. The preprocessed sequences were then assembled into contigs, or groups of overlapping sequences. Contigs were assembled using PHRAP (phragment assembly program, Phil Green, University of Washington) using default assembly parameters.

A total of 494 contigs were obtained and contig sequences were recognized as those sequences whose designations begin with Xb4695.C. All contig sequences were run through the annotation and gene selection processes as described in Example 4 below. The contig sequences were listed in the Sequence Listing file from SEQ ID NO:16425 to SEQ ID NO:16918.

Example 4

This example illustrates the identification and annotations of different genes within the 494 contigs assembled as described in Example 3. FGENESB gene prediction algorithm (Softberry, Inc., Mount Kisco, N.Y.) was used for this purpose. The genes and partial genes embedded in such contigs were identified through a series of bioinformatic analyses following the instructions as described in the program. The *X. nematophila* genome from strain Xs86068, as assembled from LIB4695, consisted of 494 sequence contigs. The sequence contigs were annotated to identify genes and gene regulation elements. As a result, 6108 protein-coding genes (SEQ ID NO:1 through SEQ ID NO:6108), 2651 promoters (SEQ ID NO:12217 through SEQ ID NO:14867), 1475 terminators (SEQ ID NO:14868 through SEQ ID NO:16342) and 82 ribosomal and transfer RNA genes (SEQ ID NO:16343 through SEQ ID NO:16424) were identified.

The *Xenorhabdus* genome was annotated by searching for homology to genes of known functions. These searches were done using homology to whole protein using blast as well as similarity to protein domains using Pfam and Hidden Markov Model algorithms. The annotations were then associated with the genes. The genome annotation was completed with FGENESB, a bacterial gene/operon prediction and annotation pipeline developed by Softberry Inc. (Mount Kisco, N.Y., USA). The annotation database and parameters were updated and customized when processing *X. nematophila* genome. These annotations were assembled into a database that could be queried by searching for key words using wildcard text searches.

The analysis was done by performing keyword searches against the annotated genome sequences in the database. Since *Xenorhabdus* is an insect pathogen, it may contain potent insecticidal molecules that are similar to the toxin complex (tc) toxins previously shown to be associated with *Photorhabdus*. There may be many genes that are associated with virulence and pathogenesis in other eukaryotes. These may include, for example, hemolysins, lipases, and RTX (repeats in toxin) family of cytolytic toxins. Homologs of histone, proteins sequestering iron, polyketides and Non-ribosomal (NRP) peptides, etc., were also searched for homology to genes of known functions. The exemplary key words used to conduct the searches included tc, toxin, RTX, PapA, hemolysin, lipase, chitinase, protease, ferritin, iron, chelin, pyoverdin, resistance, restriction, insect, *Drosophila*, ketide, NRP, polyketides, non-ribosomal, polymer, nema and nematode, etc. A wild card was used with all searches.

The search results have shown that the *Xenorhabdus* strain Xs86068 has proteins that are homologous to many important known proteins or polypeptides. The search for homologs has also led to some new discoveries. Discovery of histone homologs was unexpected as histones were not previously found in bacteria. These genes might make histones that would affect an insect's growth and development by disrupting its normal cellular processes. A PapA homolog was identified in this sequence pool. PapA has been demonstrated to have an insecticidal activity (Khandelwal et al., Biochem. Biophy. Res. Commun. 314: 943-949, 2004). The first step was done to look for any annotation containing the word "resistance" and put them into first class. Often these homologs referred to resistance to metals (e.g. tellurite resistance) or antibiotics (e.g. tetracycline resistance). Resistance homologs may also came about from small phage-like particles called colicins. These proteins may often be evolved from phage tails. Polyketides and non-ribosomal (NRP) peptides were very large proteins, often greater than 1000 amino acid residues. Proteins that affected fungi and insect skeletons included chitinases. Proteins sequestering iron were often a virulence determinant. Homologs identified included ferritin.

In summary, the nucleotide sequences identified in SEQ ID NO:1 through SEQ ID NO:12216 encode many useful *Xenorhabdus* polypeptides or proteins, including but not limited to insect inhibitory polypeptides or proteins as set forth in SEQ ID NO's 6903, 6904, 6905, 7110, 7179, 7776, 7777, 7803, 8275, 8277, 8279, 8280, 8281, 8454, 8468, 8595, 9946, 10477, 10481, 10482, 10483, 10484, 10485, 10486, 10487, 10488, 10551, 11147, 11688, 11690, 11691, 11692 and 11693; a PapA protein as set forth in SEQ ID NO:7514; hemolysin lipase protein homologues set forth in SEQ ID NO's: 6531, 6578, 6696, 7505, 7679, 7793, 7939, 8216, 8220, 8222, 8366, 8745, 9199, 9212, 10143, 10306, 10325, 10683, 10919, 10995, 10996, 11246, 11991 and 12000; polyketide synthases as set forth in SEQ ID NO's: 7253, 8852, 8857, 8864, 9558, 9560, 11014, 11583, 11587, 12090 and 12112; protease homologs as set forth in SEQ ID NO's 6308, 6309, 6310, 6393, 6537, 6549, 6595, 6774, 6941, 6942, 7199, 7289, 7328, 7503, 7627, 7682, 7683, 7749, 8152, 8300, 8301, 8870, 8957, 9108, 9263, 9265, 9296, 9319, 9343, 9720, 9725, 9748, 9749, 9884, 10246, 10385, 10461, 10588, 10614, 10896, 11020, 11830, 11831 and 11901; chitinases as set forth in SEQ ID NO's 6902, 6906, 7325, 8047 and 10542; restriction enzymes as set forth in SEQ ID NO's 8941, 8945, 9353, 11041, 11042, 11113 and 11114; histone homologues as set forth in SEQ ID NO's 6182, 7457, 7980, 8272, 8605, 8765, 8778, 8861, 9590, 9802, 10293, 10449, 10469, 10762, 10812, 10926, 11206, 11677 and 12135; ferritin homologues as set forth in SEQ ID NO's 6267, 6268 and 9272; drug metabolite transporter protein homologues set forth in SEQ ID NO's 6836, 6837, 7447, 8274, 8701, 9071, 9100, 9579, 10205, 10446, 10456, 10604, 10737 and 11018; polypeptides or proteins capable of conferring resistance to heavy metals or other toxic compositions as set forth in SEQ ID NO's 7432, 7741, 8701, 8706, 8828, 8829, 9071, 9181, 9271, 10600 and 11018; RTX (repeats in toxin) homologues as set forth in SEQ ID NO's: 9946, 10551 and 10643; a pyoverdin protein homologue as set forth in SEQ ID NO: 6598; a Zinc finger protein homologue as set forth in SEQ ID NO: 8011; an enterochelin protein homologue as set forth in SEQ ID NO: 8528; nonribosomal peptide homologues as set forth in SEQ ID NO's: 6870, 7462, 7463, 8248, 8339, 8492, 8530, 8546, 8547, 8856, 8860, 8863, 9225, 9226, 9227, 9552, 10073, 10506, 10726, 11003, 11004, 11005, 11012, 11013, 11015, 11584, 11585, 11588, 11590, 11591, 11844, 11845, 12085 and 12089; and a protein homologue to proteins from *Drosophila* species as set forth in SEQ ID NO: 7909. These proteins or polypeptides, offered by way of illustration and not by way of limitation, are just some of the exemplary proteins or peptides from the *Xenorhabdus* strain Xs86068 that are homologous to known proteins or polypeptides.

Example 5

*Xenorhabdus* strain Xs86068 was evaluated for its insecticidal activities using the following procedure. Strain 86068 was evaluated with other two *Xenorhabdus* strains Xs86830 (isolated from *Galleria melonella*) and Xs86832 (isolated from beet armyworm, BAW, *Spodotera exigua*) for comparative purpose. Specifically, three 250 mL baffled flasks each containing 50 mL BHI medium were each inoculated with 1.5 mL bacterial stock culture from each strain, respectively, and incubated at 25° C. and 280 rpm on a rotary shaker in the dark for 48 hours. The culture broth was centrifuged at 2600×g for 30 minutes at 4° C. and decanted from the cell and debris pellet. The broth was then sterile-filtered (0.2 μm) and dialyzed. The culture supernatant was concentrated 5× and was then used for bioassays to evaluate insect inhibitory properties. Five milliliter of the supernatant was applied to each insect larva for bioassay and the larvae were obtained using insect eggs obtained from commercial sources, hatched and reared using conventional methods known in the art.

Insect inhibitory activities of these strains were evaluated against members of the insects in the orders Coleoptera that included Western corn rootworm (WCR, *Diabrotica virgifera virgifera*) and cotton boll weevil (BWV, *Anthomonas grandis grandis*), Lepidoptera that included tobacco budworm (TBW, *Heliothis virescens*), corn earworm (CEW, *Helicoverpa zea*), black cutworm (BCW, *Agrotis epsilon*), and Hemiptera that included Western tarnished plant bug (WTPB, *Lygus hespus*). Insect inhibitory activity against Western corn rootworm larvae was evaluated as follows. *Xenorhabdus* culture supernatant, control medium (BHI) or Tris buffer, pH 7.0, was applied to the surface (about 0.38 cm$^2$) of a modified artificial diet (BIOSERV™; diet product F9757) in 20 μL aliquots. The plates were allowed to air-dry in a drying chamber (16-20° C.; 40-50% RH) and the wells were infested with single non-diapausing neonate WCR hatched from surface disinfested eggs (Pleau, Master of Science Thesis, Saint Louis University, 1999). Plates were sealed, placed in a humidified growth chamber and maintained at 27° C. for the appropriate period (5-7 days). Mortality and stunting (0-3) scores were then assessed and statistically analyzed (SAS institute, user's manual for JMP version 3.2, 1989-1997). Twenty four insects per treatment were used in all studies. Control mortality was generally less than 10%.

Insect inhibitory activity against Lepidopteran larvae was tested as follows. *Xenorhabdus* culture supernatant, control medium (BHI) and Tris buffer, pH 7.0, were applied directly to the surface (about 0.38 cm$^2$) of standard artificial Lepidopteran diet (Southland Products Incorporated, Lake Village, AR; Lepidopteran multi-species diet) in 20 µL aliquots. The diet plates were allowed to air-dry in a drying chamber (16-20° C.; 40-50% RH). The test wells were then infested with insect eggs of TBW, CEW or BCW suspended in agar. In the case of ECB, neonates were hand infested into the wells at one neonate per well. Following infestation, diet plates were sealed, placed in a humidity controlled growth chamber and maintained in the dark at 27° C. for the appropriate period of time. Mortality and stunting measurements were scored at day 5 and statistically analyzed (SAS institute, 1989-1997, User's manual for JMP version 3.2). Generally 24 insects per treatment were used in all studies. Control mortality generally ranged from 0-12.5%.

Insect inhibitory activity against the cotton boll weevil was evaluated as follows. *Xenorhabdus* supernatant, control medium (BHI) or Tris, pH 7.0, were applied in 20 µL aliquots to the surface of 200 µL of artificial diet (Bioserv™ Co., Frenchtown, N.J.; diet product F9247) and allowed to air-dry. Boll weevil eggs were then placed into the wells, the wells sealed and the plates held at 27° C., 60% relative humidity (RH) for 6 days. An activity score, based on confounding of gross production, growth and mortality, was then assessed and analyzed statistically (SAS institute, ibid). Control mortality ranged between 0% and 25%.

Insect inhibitory activity was also tested against *Lygus* bugs (Western Tarnished Plant Bug (WTPB), *Lygus hesperus* Knight) in the order Hemiptera. The insect inhibitory activity against *Lygus* bug was tested as follows. Feeding domes were made using a dome-making machine manufactured by Analytical Research Systems (Gainesville, Fla.). Briefly, the system used a vacuum to form domes from PARAFILM™ sheeting using an aluminum block template shaped in the form of a 96-well microtiter-plate. To each such formed dome was added 40 uL of a 1:10 (v/v) dilution of test solution in diet. The dome-molded PARAFILM™ was then heat sealed with a sheet of Mylar. The resulting PARAFILM™ dome sheet (96-wells) was placed onto a 96-well flat-bottomed microtiter plate containing one *Lygus* nymph per well. The assay was typically scored after 4 days for mortality and stunting, using a scale of 0 (no mortality or stunting) to 3 (complete mortality).

The bioassay results demonstrated that the culture supernatant containing insecticidal proteins from *X. nematophila*, strain Xs86068, exhibited insecticidal activity against some of the insect species tested. Specifically, the culture supernatant exhibited very strong insecticidal activity against WCR, BWV and WTPB. All strains showed very strong stunting effects against BWV and, among them, strain Xs86068 showed the strongest stunting effect. Similarly, all strains showed high mortality rates and, among them, strain Xs86068 showed 100% mortality rate. However, while other two strains demonstrated much lower mortality effects against WTPB, the strain Xs86068 gained the highest mortality rate (90.5%). The overall insecticidal activity of strain Xs86068 against BWV and WCR were comparable to the activities of strains Xs86830 and Xs86832. Strain Xs86068 seemed to be more active against WTPB in comparison to strains Xs86830 and Xs86832. Therefore, the bioassays using the cultural supernatant exhibited insecticidal activities against WCR, BWV and WTPB, but not against TBW, CEW and BCW.

In the other bioassay conducted, similar results were observed. The strain Xs86068 was tested against WCR and WTPB as 1× unprocessed supernatant from a 48 h shaken culture (BHI medium, 25° C.). The culture was used as un-heated, heated (boiled 20 min.), and concentrated 5-fold (3K MWCO). The untreated 1× culture was most active against WCR with 100% mortality rate and the highest stunting effect rated as number 3. Similarly, the untreated 1× culture was most active against WTPB with 90% mortality rate (stunting rate unavailable). Heating process destroyed the insecticidal activity against WCR with 0% mortality rate but only decreased the insecticidal activity against WTPB with 49% mortality. Concentration of the supernatant by 5-fold decreased the insecticidal activity on both the insects with 12% mortality on WCR and 82% mortality on WTPB. Therefore, the insecticidal activity against WCR and WTPB seems to be heat-labile.

The specification above describes exemplary embodiments of the present invention. It will be understood by those skilled in the art that, without departing from the scope and spirit of the present invention and without undue experimentation, the present invention can be performed within a wide range of equivalent parameters. While the present invention has been described in connection with specific embodiments, it will be understood that it is capable of further modifications. Various permutations and combination of the elements provided in all the claims that follow are possible and fall within the scope of this invention.

SEQ ID NO's referred to herein are listed in the sequence listing on CD-ROM which accompanies this specification. All patent publications referred to in this specification are incorporated herein by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07319142B1). An electronic copy of the "Sequence Listing" will also be available from the USPTO upon request and payment of the fee set forth in 37 CFR 1.19(b)(3).

What is claimed is:

1. An isolated nucleotide sequence encoding a *Xenorhabdus nematophila* strain Xs86068 protein, wherein said protein comprises the amino acid sequence set forth in SEQ ID NO:6903.

2. The isolated nucleotide sequence of claim 1, comprising the sequence set forth in SEQ ID NO:795.

3. The isolated nucleotide sequence of claim 2, said *Xenorhabdus nematophila* strain Xs86068 having an NRRL deposit number B-30757.

* * * * *